(12) United States Patent
Caruso

(10) Patent No.: US 6,562,835 B1
(45) Date of Patent: May 13, 2003

(54) METHOD FOR THE TREATMENT OF URINARY INCONTINENCE

(75) Inventor: Frank S. Caruso, Colts Neck, NJ (US)

(73) Assignee: Endo Pharmaceuticals Inc., Chadds Ford, PA (US)

( * ) Notice: Subject to any disclaimer, the term of this patent is extended or adjusted under 35 U.S.C. 154(b) by 1520 days.

(21) Appl. No.: 08/734,738

(22) Filed: Oct. 21, 1996

Related U.S. Application Data

(62) Division of application No. 08/398,389, filed on Mar. 3, 1995.

(51) Int. Cl.[7] .................. A61P 13/00; A61K 31/485; A61K 9/22; A61K 9/52
(52) U.S. Cl. .................. 514/289; 514/963; 514/964; 424/457; 424/468
(58) Field of Search .................. 514/289, 963–4; 424/457, 468

(56) References Cited

U.S. PATENT DOCUMENTS

| | | | | |
|---|---|---|---|---|
| 4,316,888 A | * | 2/1982 | Nelson | |
| 4,738,966 A | * | 4/1988 | Sunshine et al. | 514/277 |
| 4,898,860 A | * | 2/1990 | Musacchio et al. | |
| 5,192,751 A | * | 3/1993 | Thor | 514/82 |
| 5,321,012 A | * | 6/1994 | Mayer et al. | 514/25 |

* cited by examiner

Primary Examiner—Edward J. Webman
(74) Attorney, Agent, or Firm—Dilworth & Barrese, LLP

(57) ABSTRACT

Urinary incontinence is alleviated in a mammal by administering to the mammal a urinary incontinence alleviating amount of dextromethorphan, dextrorphan, their mixtures and/or pharmaceutically acceptable salts, alone or in combination with a pharmacologically active agent such as an anticholinergic, sympathomimetic, tricyclic antidepressant, antispasmodic, direct-acting smooth muscle relaxant, estrogen, compound having estrogen-like activity, or any combination of the foregoing.

8 Claims, 1 Drawing Sheet

METHOD FOR THE TREATMENT OF URINARY INCONTINENCE

This is a divisional of copending application Ser. No. 08/398,389 filed Mar. 3, 1995.

BACKGROUND OF THE INVENTION

1. Field of the Invention

The present invention relates to a method for treating urinary incontinence.

2. Description of Related Art

Urinary incontinence is a fairly common medical problem in which urine is involuntarily lost. Urinary incontinence may be transient or persistent. Common causes of transient urinary incontinence include infection, atrophic urethritis, administration of diuretics and delirium. Persistent urinary incontinence is classified into four types: (1) stress incontinence which involves involuntary loss of urine during coughing, sneezing, laughing, or other physical activity; (2) urge incontinence which involves involuntary loss of urine associated with an abrupt or strong desire to void; (3) overflow incontinence which involves involuntary loss of urine associated with over-distension of the bladder; and (4) mixed incontinence which involves a combination of at least two of the above types.

Persistent urinary incontinence can result from spastic or hyperactive bladder smooth muscle such as detrusor originating incontinence. In certain instances such incontinence is caused by loss of control resulting from spinal injury, parkinsonism, multiple sclerosis or recurrent bladder infection to name a few. Treatment of incontinence may involve surgery or administration of any of various pharmacological agents, e.g., a anticholinergic such as oxybutynin, atropine, propantheline, terodiline, dicyclomine and others, a sympathomimetic such as ephedrine, pseudoephedrine, phenylpropanolamine and others, a tricyclic antidepressant such as amitriptyline, imipramine, doxepin and others, an estrogen or a direct acting antispasmodic such as flavoxate. In addition to treating incontinence, such pharmacological agents may cause other powerful physiologic responses such as excitability (sympathomimetics), and dry mouth, drowsiness, dizziness or hallucinations (anticholinergics or tricyclic antidepressants).

Other compounds described as useful for treating urinary incontinence are described, e.g., in U.S. Pat. Nos. 4,645,758, 4,865,843, 5,080,905, 5,236,956, 5,233,053, 5,252,589, 5,258,390, 5,272,163, 5,340,805, 5,340,819, 5,340,826, and 5,266,596. U.S. Pat. No. 5,192,751 describes the use of certain competitive N-methyl-D-aspartate (NMDA) receptor antagonists in the treatment of urinary incontinence. It is noted therein that a non-competitive NMDA receptor antagonist, MK-801, has been reported to produce an increase in frequency in micturition (Vera et al., *Neurosci. Lett.*, 134, 135–138 (1991)).

Dextromethorphan and its main metabolite, dextrorphan, are non-competitive NMDA receptor antagonists having few, if any, side effects at indicated dosage levels. Dextromethorphan and dextrorphan have been used as antitussives, for treatment of chronic pain (U.S. Pat. No. 5,352,683) and for inhibiting the development of tolerance to and/or dependence on a narcotic analgesic (U.S. Pat. No. 5,321,012). Surprisingly, it has now been found that the non-competitive NMDA receptor antagonists dextromethorphan and dextrorphan are useful in the treatment of urinary incontinence.

SUMMARY OF THE INVENTION

In accordance with the present invention, there is provided a method for the treatment of urinary incontinence which comprises administering to a mammal exhibiting urinary incontinence a urinary incontinence alleviating amount of at least one morphinan selected from the group consisting of dextromethorphan, dextrorphan and pharmaceutically acceptable salts thereof. The method can optionally include administration of one or more pharmacologically active agents selected from the group consisting of anticholinergics, sympathomimetics, tricyclic antidepressants, antispasmodics, direct acting bladder smooth muscle relaxants, estrogens, compounds having estrogen-like activity, and any combination of the foregoing.

In another embodiment of the present invention, there is provided a method of decreasing micturition frequency in a mammal which comprises administering to a mammal a micturition decreasing amount of at least one morphinan selected from the group consisting of dextromethorphan, dextrorphan and pharmaceutically acceptable salts thereof. The method can optionally include administration of any of the pharmacologically active agents mentioned above.

DESCRIPTION OF THE PREFERRED EMBODIMENTS

Figure 1:
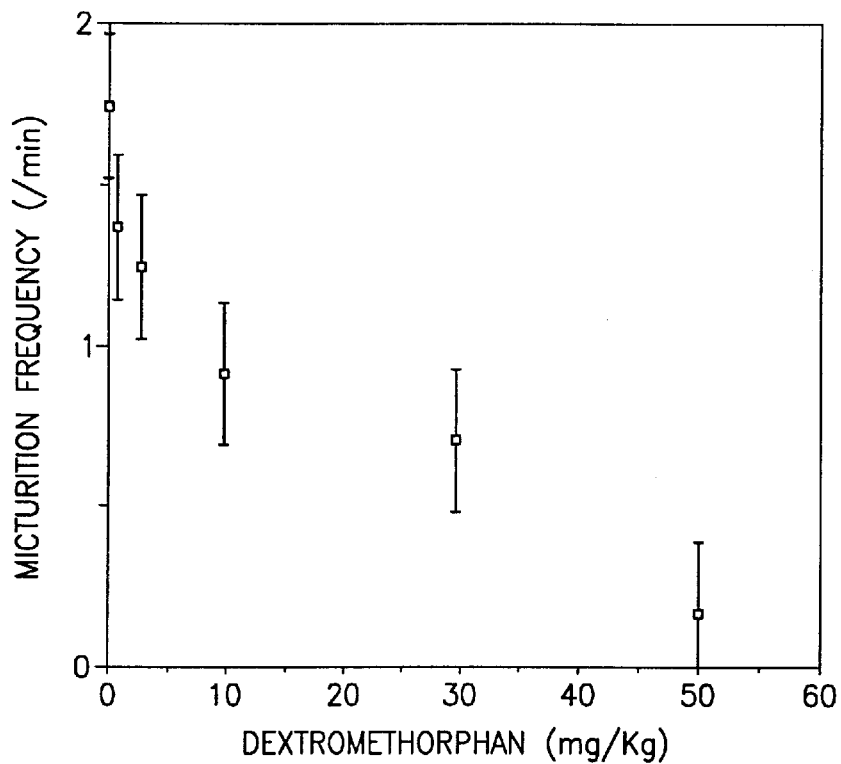
FIG. 1 is a graphical representation of test results showing therapeutic effects of intravenous administration of dextromethorphan on absolute micturition pressures in rats; and, FIG. 2 is a graphical representation of test results showing therapeutic effects of intravenous administration of dextromethorphan on micturition frequency in rats.

Dextromethorphan ((+)-3-methoxy-N-methylmorphinan) and dextrorphan ((+)-3-hydroxy-N-methylmorphinan), their mixtures and pharmaceutically acceptable salts are utilized in accordance with the method of the present invention. Accordingly, dextromethorphan, dextrorphan, their mixtures and/or pharmaceutically acceptable salts are administered by any known route of administration for the relief of symptoms of bladder instability associated with voiding in patients with uninhibited neurogenic or reflex neurogenic bladder such as urgency, frequency, urine leakage, urge incontinence, stress incontinence, overflow incontinence, mixed incontinence or dysuria. Dextromethorphan, dextrorphan, their mixtures and/or pharmaceutically acceptable salts are also useful in the treatment of interstitial cystitis, a chronic inflammatory condition of unknown etiology resulting in reduced bladder capacity and severe bladder irritative symptoms. Administration of dextromethorphan, dextrorphan, their mixtures and/or pharmaceutically acceptable salts acts to quiet the bladder and reduce the frequency of micturition.

Administration of dextromethorphan, dextrorphan their mixtures and/or pharmaceutically acceptable salts can be orally or transdermally or by intravenous, intramuscular, subcutaneous, intrathecal, epidural or intracerebroventricular injection. Effective dosage levels can vary widely, e.g., from about 0.25 to about 250 mg/day, but actual amounts will, of course, depend on the state and circumstances of the patient being treated. As those skilled in the art recognize, many factors that modify the action of the active substance herein will be taken into account by the treating physician such as the age, body weight, sex, diet and condition of the patient, the time of administration, the rate and route of administration, and so forth. Optimal dosages for a given set of conditions can be ascertained by those skilled in the art using conventional dosage determination tests in view of the experimental data provided herein.

Therapeutic compositions containing dextromethorphan, dextrorphan, their mixtures and/or pharmaceutically acceptable salts will ordinarily be formulated with one or more pharmaceutically acceptable ingredients in accordance with known and established practice. Thus, dextromethorphan, dextrorphan, their mixtures and/or pharmaceutically acceptable salts can be formulated as a liquid, powder, elixir, injectable solution, etc. Formulations for oral use can be provided as hard gelatin capsules wherein dextromethorphan, dextrorphan, their mixtures and/or pharmaceutically acceptable salts are mixed with an inert solid diluent such as calcium carbonate, calcium phosphate or kaolin, or as soft gelatin capsules wherein dextromethorphan, dextrorphan, their mixtures and/or pharmaceutically acceptable salts are mixed with an oleaginous medium, e.g., liquid paraffin or olive oil.

Aqueous suspensions can contain the dextromethorphan, dextrorphan, their mixtures and/or pharmaceutically acceptable salts in admixture with pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g, heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

Dispersible powders and granules suitable for preparation of an aqueous suspension by the addition of water provide dextromethorphan, dextrorphan, their mixtures and/or pharmaceutically acceptable salts in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, can also be present. Syrups and elixirs can be formulated with sweetening agents, for example glycerol, sorbitol or sucrose. Such formulations can also contain a demulcent, a preservative and flavoring and coloring agents.

Dextromethorphan, dextrorphan, their mixtures and/or pharmaceutically acceptable salts are advantageously provided in sustained release dosage form of which many kinds are known, e.g., as described in U.S. Pat. Nos. 4,788,055; 4,816,264; 4,828,836; 4,834,965; 4,834,985; 4,996,047; 5,071,646; and, 5,133,974, the contents of which are incorporated by reference herein.

It is also within the scope of this invention to administer dextromethorphan, dextrorphan, their mixtures and/or pharmaceutically acceptable salts prior to, concurrently with, or after administration of any other known pharmacologically active agent useful for treating urinary incontinence. Such agents include, but are not limited to, anticholinergics such as oxybutynin, atropine, propantheline, terodiline, dicyclomine, etc., sympathomimetics such as ephedrine, pseudoephedrine, epinephrine, phenylpropanolamine, etc., tricyclic antidepressants such as imipramine, doxepin, amitriptyline, etc., estrogens or estrogen-related compounds having estrogen-like activity such as estradiol, estrone, etc., and antispasmodics or direct acting bladder smooth muscle relaxants such as flavoxate. For a detailed discussion of these pharmacologically active agents, reference may be made to "Goodman and Gillman's Pharmacological Basis of Therapeutics", Goodman et al., eds. 7th ed., 1985, Macmillan and Company, New York.

The examples that follow are illustrative of the present invention and should not be construed as limiting.

EXAMPLE 1

Ten female Sprague-Dawley rats having a mean weight of 263±19 g were anesthetized with urethane (1.2 g/k, sc.). A midline incision was performed to expose the bladder and a 23G catheter was inserted into the bladder dome for the measurement of intravesical pressure. A non-stop transvesical cystometrogram, as described in J. Pharmacological. Methods, 15, pp. 157–167 (1986), was used, at a filling rate of 0.216 ml/min. of saline, to access the filling and voiding characteristics of the bladder. Through the continuous cystometry method thus afforded, consecutive micturition could be recorded. Dextromethorphan was given at intravenous does of: 1.0, 3.0, 10, 30, 50 mg/kg after the initial baseline micturition sequence was reliably measured for approximately 12 min. From these recordings the absolute values in maximum pressure obtained and the frequency of micturition was measured. A dose response curve illustrating the effect of dextromethorphan on the absolute micturition pressures in the range of 1–50 mg/kg is given in FIG. 1. Data given are mean and SE.

The volume evoked micturition reflex was suppressed in a dose sensitive manner as seen from the effect of increasing doses of dextromethorphan on the cystometrogram. In particular it was found that at doses in the range of 10–30 mg/kg, the volume evoked micturition contractions are almost totally suppressed. A significant sustained reduction in detrusor pressure is produced at a dose level of 3 mg/kg and a 50% reduction is evident at 10 mg/kg. As shown in FIG. 1, at higher doses of dextromethorphan, the rate of decrease in detrusor pressure is diminished. Furthermore at does higher than 10 mg/kg the effect of the drug appears to be bimodal, producing an initial increase in detrusor pressure before suppression.

Figure 2:
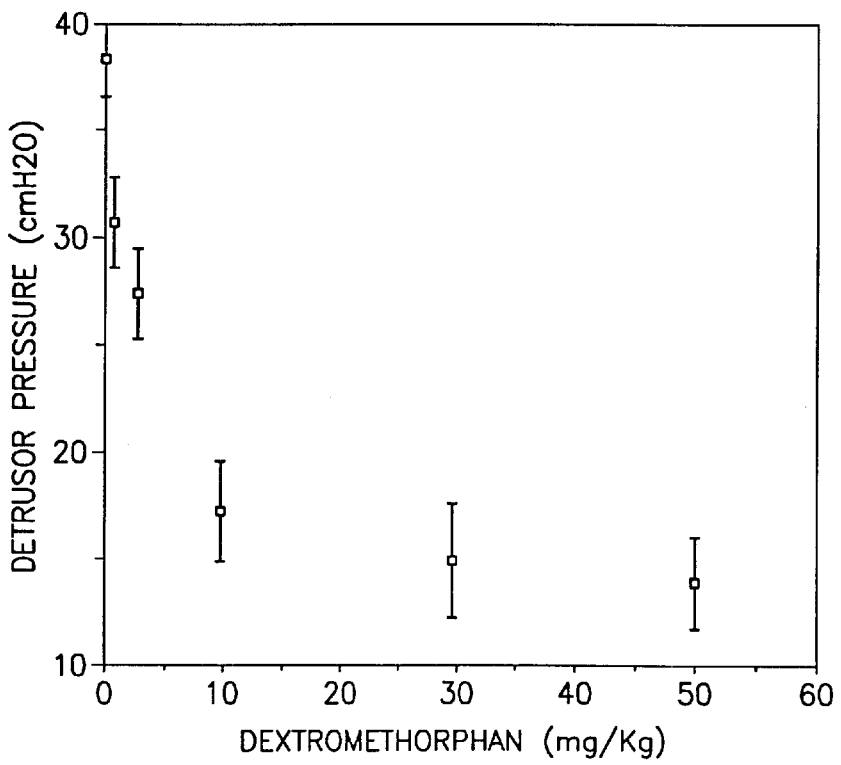

The corresponding dose response effect of dextromethorphan on the frequency of micturition is given in FIG. 2. As shown, the frequency of micturition decrements gradually with respect to dose when compared to the pressure.

EXAMPLE 2

A capsule containing dextromethorphan hydrobromide contains the following ingredients:

| Ingredient | mg/Capsule |
| --- | --- |
| Dextromethorphan Hydrobromide USP | 20 |
| Pregelatinized Starch NF | 50 |
| Colloidal Silicon Dioxide | 1.5 |

EXAMPLE 3

A tablet containing dextromethorphan hydrobromide contains the following ingredients:

| Ingredient | mg/Tablet |
|---|---|
| Dextromethorphan Hydrobromide USP | 20 |
| Microcrystalline Cellulose NF | 17 |
| Lactose NF anhydrous | 68 |
| Croscarmellose NF | 1 |
| Colloidal Silicon Dioxide | 1.5 |
| Magnesium Stearate NF | 1.5 |

EXAMPLE 4

A controlled release tablet containing dextromethorphan hydrobromide contains the following ingredients:

| Ingredient | mg/Tablet |
|---|---|
| Dextromethorphan Hydrobromide USP | 40 |
| Lactose NF | 70 |
| Methocel E 15LV | 100 |
| Ethylcellulose NF | 35 |
| Magnesium Stearate NF | 15 |
| Colloidal Silicon Dioxide NF | 2 |

The embodiments and examples given above are illustrative of the present invention. Consequently it should be understood that modifications can be made by those with ordinary skill in the art that are intended to be covered by the following claims.

What is claimed is:

1. A composition comprising at least one morphinan selected from the group consisting of dextromethorphan, dextrorphan and the pharmaceutically acceptable salts thereof and at least one pharmacologically active agent selected from the group consisting of tricyclic antidepressants, antispasmodics, direct-acting bladder smooth muscle relaxants, estrogens, compounds having estrogen-like activity, and any combination of the foregoing.

2. The composition of claim 1 in sustained release dosage form.

3. The composition of claim 1 wherein the antidepressant is selected from the group consisting of imipramine, doxepin and amitriptyline.

4. The composition of claim 1 wherein the antispasmodic is a flavoxate.

5. The composition of claim 1 wherein the compound having estrogen-like activity is selected form the group consisting of estradiol and estrone.

6. The composition of claim 3 in sustained release dosage form.

7. The composition of claim 4 in sustained release dosage form.

8. The composition of claim 5 in sustained release dosage form.

* * * * *